United States Patent [19]

Pacifici et al.

[11] Patent Number: 5,521,295
[45] Date of Patent: May 28, 1996

[54] NUCLEIC ACIDS ENCODING HYBRID RECEPTOR MOLECULES

[75] Inventors: Robert E. Pacifici; Arlen R. Thomason, both of Thousand Oaks, Calif.

[73] Assignee: Amgen Inc., Thousand Oaks, Calif.

[21] Appl. No.: 336,708

[22] Filed: Nov. 8, 1994

Related U.S. Application Data

[63] Continuation of Ser. No. 73,196, Jun. 7, 1993, abandoned.
[51] Int. Cl.$^6$ .......................... C07H 21/00; C12N 15/06; C12N 5/10; C07K 14/00
[52] U.S. Cl. ...................... 536/23.4; 435/7.1; 435/172.3; 435/320.1; 530/350
[58] Field of Search ................................ 435/7.1, 172.3, 435/320.1, 7.1; 530/350; 536/23.4

[56] References Cited

U.S. PATENT DOCUMENTS

| | | | |
|---|---|---|---|
| 4,859,609 | 8/1989 | Dull et al. ............................... | 436/50.1 |
| 5,030,576 | 7/1991 | Dull et al. ............................... | 435/69.7 |

FOREIGN PATENT DOCUMENTS

| | | | |
|---|---|---|---|
| 0244221 | 11/1987 | European Pat. Off. ........ | C07K 15/00 |
| 0533006 | 3/1993 | European Pat. Off. ........ | C12N 15/12 |

OTHER PUBLICATIONS

Seedorf et al., "Analysis of Platelet–derived Growth Factor Receptor Domain Function Using a Novel Chimeric Receptor Approach*," *The Journal of Biological Chemistry*, vol. 266, 12424–12431, Jan. 1991.
Venkitaraman and Cowling, Interleukin 7 receptor functions by recruiting the tyrosine kinase etc., *Proc. Natl. Acad. Sci. USA* vol. 89, 12083–12087, Dec. 1992.
Yan et al., Chimeric NGF–EGF Receptors Define Domains Responsible for Neuronal Differentiation, *Science*, vol. 252, 561–563 Apr. 1991.
Zon et al., The Erthropoietin Receptor Transmembrane Region etc., *Molecular and Cellular Biology*, vol. 12, No. 7, 2949–2957 Jul. 1992.
Adachi et al., Identification of a domain of $ET_A$ receptor required for ligand binding, *FEBS Letters*, vol. 311, No. 2, 179–183, 1992.
Bernard et al., High–affinity interleukin 2 binding by an oncogenic hybrid interleukin 2–epidermal growth factor receptor molecule, *Proc. Natl. Acad. Sco. USA*, vol. 84, 2125–2129, Apr. 1987.
Fuh et al., Rational Design of Potent Antagonists to the Human Growth Hormone Receptor, *Science*, vol. 256, 1677–1680, Jun. 1992.
Koller et al., Conservation of the Kinaselike Regulatory Domain etc., *Molecular and Cellular Biology*, vol. 12, No. 6, 2581–2590 Jun. 1992.
Lev et al., Receptor Functions and Ligand–Dependent Transforming Potential of a Chimeric etc., *Molecular and Cellular Biology*, vol. 10, No. 11, 6064–6068, Nov. 1990.
Luyten and Leysen, Receptor cloning and heterologous expression–towards a new tool for drug discovery, *TIBTECH* reviews vol. 11, 247–254, Jun. 1993.
Ohashi et al., Ligand–induced activation of chimeric receptors between the erythoropoietin receptor and receptor tyrosine kinases, *Proc. Nat'l Acad. Sci. USA*, vol. 91, pp. 158–162, Jan. 1994.
Pacifici et al., Hybrid Tyrosine Kinase/Cytokine Receptors Transmit Mitogenic Signals in Response to Ligand, *Journal of Biological Chemistry*, vol. 269, No. 3, Issue of Jan. 21, 1994, pp. 1571–1574.
Maruyama et al., Proliferation and Erythroid Differentiation through the Cytoplasmic Domain of the Erythropoietin Receptor, *Journal of Biological Chemistry*, vol. 269, No. 8, Issue of Feb. 25, 1994, pp. 5976–5980.
Riedel et al., A Chimaeric Receptor Allows Insulin to Stimulate Tyrosine Kinase Activity of Epidermal Growth Factor Receptor, *NATURE*, vol. 324, 6 Nov. 1986, pp. 68–70.

*Primary Examiner*—W. Gary Jones
*Assistant Examiner*—David Schreiber
*Attorney, Agent, or Firm*—Nancy Oleski

[57] ABSTRACT

Provided are hybrid receptor molecules wherein one domain of the receptor is derived from the cytokine superfamily of receptors and other domain is derived from a heterologous family of receptors. Also provided are methods for identifying ligands that bind to the hybrid receptor molecules.

5 Claims, 3 Drawing Sheets

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:1:

AAGATCAAAG TGCTGGGCTC CGGT    24

( 2 ) INFORMATION FOR SEQ ID NO:2:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:2:

ATGGTATTCT TTCTCTTCCG C    21

( 2 ) INFORMATION FOR SEQ ID NO:3:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:3:

GCCAACGCCA CAACCACCGC GCGCGGCCGC CTGACTCCG    39

( 2 ) INFORMATION FOR SEQ ID NO:4:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:4:

TGAGAGACAG CGTCAATATT AGCGGGATCT TAGGCCCATT    40

( 2 ) INFORMATION FOR SEQ ID NO:5:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:5:

AATGGGCCTA AGATCCCGCT AATATTGACG CTGTCTCTCA    40

( 2 ) INFORMATION FOR SEQ ID NO:6:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:6:

AGCAGCCACA GCTGGAAGTT AC    22

( 2 ) INFORMATION FOR SEQ ID NO:7:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:7:

ACTCCAGAAT CCGCTGAAGC TCGGGATCTT AGGCCCATT    39

( 2 ) INFORMATION FOR SEQ ID NO:8:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:8:

AATGGGCCTA AGATCCCGAG CTTCAGCGGA TTCTGGAGT    39

( 2 ) INFORMATION FOR SEQ ID NO:9:

( i ) SEQUENCE CHARACTERISTICS:
        ( A ) LENGTH: 644 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:9:

```
Met Arg Pro Ser Gly Thr Ala Gly Ala Ala Leu Leu Ala Leu Leu Ala
 1               5                  10                  15

Ala Leu Cys Pro Ala Ser Arg Ala Leu Glu Glu Lys Lys Val Cys Gln
             20                  25                  30

Gly Thr Ser Asn Lys Leu Thr Gln Leu Gly Thr Phe Glu Asp His Phe
             35                  40                  45

Leu Ser Leu Gln Arg Met Phe Asn Asn Cys Glu Val Val Leu Gly Asn
     50                  55                  60

Leu Glu Ile Thr Tyr Val Gln Arg Asn Tyr Asp Leu Ser Phe Leu Lys
 65                  70                  75                  80

Thr Ile Gln Glu Val Ala Gly Tyr Val Leu Ile Ala Leu Asn Thr Val
                 85                  90                  95

Glu Arg Ile Pro Leu Glu Asn Leu Gln Ile Ile Arg Gly Asn Met Tyr
             100                 105                 110

Tyr Glu Asn Ser Tyr Ala Leu Ala Val Leu Ser Asn Tyr Asp Ala Asn
             115                 120                 125

Lys Thr Gly Leu Lys Glu Leu Pro Met Arg Asn Leu Gln Glu Ile Leu
     130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
             180                 185                 190

Ser Cys Pro Asn Gly Ser Cys Trp Gly Ala Gly Glu Glu Asn Cys Gln
     195                 200                 205

Lys Leu Thr Lys Ile Ile Cys Ala Gln Gln Cys Ser Gly Arg Cys Arg
 210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
             245                 250                 255

Glu Ala Thr Cys Lys Asp Thr Cys Pro Pro Leu Met Leu Tyr Asn Pro
             260                 265                 270

Thr Thr Tyr Gln Met Asp Val Asn Pro Glu Gly Lys Tyr Ser Phe Gly
             275                 280                 285

Ala Thr Cys Val Lys Lys Cys Pro Arg Asn Tyr Val Val Thr Asp His
     290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
             325                 330                 335

Cys Asn Gly Ile Gly Ile Gly Glu Phe Lys Asp Ser Leu Ser Ile Asn
             340                 345                 350

Ala Thr Asn Ile Lys His Phe Lys Asn Cys Thr Ser Ile Ser Gly Asp
         355                 360                 365

Leu His Ile Leu Pro Val Ala Phe Arg Gly Asp Ser Phe Thr His Thr
     370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
             405                 410                 415

Leu His Ala Phe Glu Asn Leu Glu Ile Ile Arg Gly Arg Thr Lys Gln
             420                 425                 430
```

| | | | | | | | | | | | | | | |
|---|---|---|---|---|---|---|---|---|---|---|---|---|---|---|
|His|Gly|Gln<br>435|Phe|Ser|Leu|Ala|Val<br>440|Val|Ser|Leu|Asn|Ile<br>445|Thr|Ser|Leu|
|Gly|Leu<br>450|Arg|Ser|Leu|Lys|Glu<br>455|Ile|Ser|Asp|Gly|Asp<br>460|Val|Ile|Ile|Ser|
|Gly<br>465|Asn|Lys|Asn|Leu|Cys<br>470|Tyr|Ala|Asn|Thr|Ile<br>475|Asn|Trp|Lys|Lys|Leu<br>480|
|Phe|Gly|Thr|Ser|Gly<br>485|Gln|Lys|Thr|Lys|Ile<br>490|Ile|Ser|Asn|Arg|Gly<br>495|Glu|
|Asn|Ser|Cys|Lys<br>500|Ala|Thr|Gly|Gln|Val<br>505|Cys|His|Ala|Leu|Cys<br>510|Ser|Pro|
|Glu|Gly|Cys<br>515|Trp|Gly|Pro|Glu|Pro<br>520|Arg|Asp|Cys|Val|Ser<br>525|Cys|Arg|Asn|
|Val|Ser<br>530|Arg|Gly|Arg|Glu|Cys<br>535|Val|Asp|Lys|Cys|Lys<br>540|Leu|Leu|Glu|Gly|
|Glu<br>545|Pro|Arg|Glu|Phe|Val<br>550|Glu|Asn|Ser|Glu|Cys<br>555|Ile|Gln|Cys|His|Pro<br>560|
|Glu|Cys|Leu|Pro|Gln<br>565|Ala|Met|Asn|Ile|Thr<br>570|Cys|Thr|Gly|Arg|Gly<br>575|Pro|
|Asp|Asn|Cys|Ile<br>580|Gln|Cys|Ala|His|Tyr<br>585|Ile|Asp|Gly|Pro|His<br>590|Cys|Val|
|Lys|Thr|Cys<br>595|Pro|Ala|Gly|Val|Met<br>600|Gly|Glu|Asn|Asn|Thr<br>605|Leu|Val|Trp|
|Lys|Tyr|Ala<br>610|Asp|Ala|Gly|His|Val<br>615|Cys|His|Leu|Cys|His<br>620|Pro|Asn|Cys|
|Thr<br>625|Tyr|Gly|Cys|Thr|Gly<br>630|Pro|Gly|Leu|Glu|Gly<br>635|Cys|Pro|Thr|Asn|Gly<br>640|
|Pro|Lys|Ile|Pro|

(2) INFORMATION FOR SEQ ID NO:10:

(i) SEQUENCE CHARACTERISTICS:
        (A) LENGTH: 258 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:10:

| | | | | | | | | | | | | | | |
|---|---|---|---|---|---|---|---|---|---|---|---|---|---|---|
|Leu<br>1|Ile|Leu|Thr|Leu<br>5|Ser|Leu|Ile|Leu|Val<br>10|Leu|Ile|Ser|Leu|Leu<br>15|Leu|
|Thr|Val|Leu|Ala<br>20|Leu|Leu|Ser|His|Arg<br>25|Arg|Thr|Leu|Gln|Gln<br>30|Lys|Ile|
|Trp|Pro|Gly<br>35|Ile|Pro|Ser|Pro|Glu<br>40|Ser|Glu|Phe|Glu|Gly<br>45|Leu|Phe|Thr|
|Thr|His<br>50|Lys|Gly|Asn|Phe|Gln<br>55|Leu|Trp|Leu|Leu|Gln<br>60|Arg|Asp|Gly|Cys|
|Leu<br>65|Trp|Trp|Ser|Pro|Gly<br>70|Ser|Ser|Phe|Pro|Glu<br>75|Asp|Pro|Pro|Ala|His<br>80|
|Leu|Glu|Val|Leu|Ser<br>85|Glu|Pro|Arg|Trp|Ala<br>90|Val|Thr|Gln|Ala|Gly<br>95|Asp|
|Pro|Gly|Ala|Asp|Asp<br>100|Glu|Gly|Pro|Leu|Leu<br>105|Glu|Pro|Val|Gly|Ser<br>110|Glu|
|His|Ala|Gln|Asp|Thr<br>115|Tyr|Leu|Val|Leu|Asp<br>120|Lys|Trp|Leu|Leu|Pro<br>125|Arg|
|Thr|Pro|Cys|Ser|Glu|Asn|Leu|Ser|Gly|Pro|Gly|Gly|Ser|Val|Asp|Pro|

```
                130                         135                         140
        Val Thr Met Asp Glu Ala Ser Glu Thr Ser Ser Cys Pro Ser Asp Leu
        145                     150                 155                 160
        Ala Ser Lys Pro Arg Pro Glu Gly Thr Ser Pro Ser Ser Phe Glu Tyr
                        165                     170                 175
        Thr Ile Leu Asp Pro Ser Ser Gln Leu Leu Cys Pro Arg Ala Leu Pro
                    180                 185                 190
        Pro Glu Leu Pro Pro Thr Pro Pro His Leu Lys Tyr Leu Tyr Leu Val
                195                 200                 205
        Val Ser Asp Ser Gly Ile Ser Thr Asp Tyr Ser Ser Gly Gly Ser Gln
            210             215                 220
        Gly Val His Gly Asp Ser Ser Asp Gly Pro Tyr Ser His Pro Tyr Glu
        225             230                 235                     240
        Asn Ser Leu Val Pro Asp Ser Glu Pro Leu His Pro Gly Tyr Val Ala
                        245                 250                 255
        Cys Ser
```

NUCLEIC ACIDS ENCODING HYBRID RECEPTOR MOLECULES

This application is a continuation of application Ser. No. 08/073,196, filed Jun. 7, 1993 abandoned which is hereby incorporated by reference.

FIELD OF THE INVENTION

This invention relates to biologically active hybrid receptor molecules. More specifically, the invention is directed to receptor molecules that are hybrids of a receptor extracellular domain and a receptor intracellular domain, where one of the domains is derived from certain members of the hematopoietic cytokine family of receptors, and the other domain is derived from an unrelated family of receptors.

DESCRIPTION OF RELATED ART

Growth and differentiation of cells occurs by a variety of mechanisms. One common mechanism is via a cellular response to certain extracellular chemical or physical stimuli. Some of the chemical stimuli are known as ligands. Ligands bind to specific receptors on the cellular membrane, thereby ultimately resulting in the transition of a signal to the cell or other response.

The receptors are typically proteinaceous macromolecules that span a particular cell membrane. Most receptors possess three domains, the extracellular domain, the transmembrane spanning domain, and the intracellular domain. The extracellular domain of the receptor usually serves as the binding site for the ligand, the transmembrane or membrane spanning domain typically serves to anchor the receptor into the membrane, and the intracellular domain often serves to transmit a signal to the intracellular environment.

Signal transduction appears to occur in a variety of ways upon ligand binding, such as for example, by a conformational change in the structure of the receptor, by dimerization of two identical or related receptor-type molecules, or by internalization of the ligand (see, Schlessinger et al., *Neuron*, 9:383–391 [1992]; Vairo et al., *Immunol. Today*, 12:362–369 [1991]; Ullrich et al., *Cell*, 61:203–212 [1990]; Hatakeyama et al., *J. Exp. Med.*, 166:362–375 [1987]).

Many receptors have been identified, and the scientific literature has variously divided them into groups, superfamilies, families and/or classes of receptors based on common features such as tissue distribution of the receptors, nucleic acid or amino acid homology of the receptors, mechanisms of signaling by the receptors, or the type of ligand that binds to the receptors. A uniform system of classifying or grouping receptors however, has not been used in the literature.

One group of receptors has been termed the cytokine receptor superfamily. Most cytokines are soluble proteins that affect the growth and differentiation of many cell types such as cells involved in hematopoiesis and cells involved in the immune response. Cytokines exert their effect on the growth and differentiation of cells by binding to one or more members of this superfamily of receptors. The receptors are generally located on the cell surface membrane (plasma membrane). The cytokine receptor superfamily contains many families, such as, for example, the hematopoietic receptor family, the interferon receptor (IFN-R) family, the tumor necrosis factor receptor (TNF-R) family, the nerve growth factor receptor (NGF-R) family, the transforming growth factor (TGF) beta receptor family, and the interleukin-8 (IL-8) receptor family (see Taga et al. *FASEB J.*, 6:3387–3396 [1992]).

Another separate and distinct group of receptors is the protein-tyrosine kinase receptor family. This receptor family shares the common trait of phosphorylation (via ATP hydrolysis) of the hydroxyl group of a tyrosine residue of a selected intracellular enzyme, or autophosphorylation of the receptor itself upon ligand binding to the receptor. A large number of receptors have been identified as members of this family, including, among others, epidermal growth factor receptor (EGFR), platelet derived growth factor receptor (PDGFR), and insulin receptor (IR).

Another distinct group of receptors is the atrial natriuretic peptide receptor family. This family of receptors has one or more of the atrial natriuretic peptides (ANPs) as ligands. ANP is involved in the regulation of fluids across the cellular plasma membrane. This family of receptors consists of atrial natriuretic peptide receptor A (ANPRA), atrial natriuretic peptide receptor B (ANPRB) and atrial natriuretic peptide receptor C (ANPRC). These receptors are each expressed at different levels in different types of cells (Wilcox et al., *Mol. Cell. Biol.*, 11:3454–3462 [1991]).

Still another group of receptors are those with two common characteristics: they all have seven transmembrane spanning domains, and they are all believed to transduce signals to the intracellular environment via G-proteins (GTP binding proteins). This group includes such receptors as the rhodopsin and related opsin receptors, the alpha and beta adrenergic receptors, the muscarinic cholinergic receptors, and the yeast mating factor receptors. The thrombin receptor is also known to have seven transmembrane spanning domains (see WO 92/14750).

Many other receptor groups have also been identified, such as the steroid receptor family, of which the retinoic acid receptor is a member, the family of the endothelin receptors (Adachi et al., *FEBS Lett*, 311:179–183 [1992]) and related receptors, the glutamate family of receptors, and the family containing the transferrin receptor.

Several receptors have been cloned and the DNA sequences have been obtained. In addition, mutant receptors have been generated and tested for biological activity as compared to the naturally occurring, or wild-type, receptor molecules. For example, Quelle et al., (*Mol. Cell. Biol.*, 12:4553–4561 [1992]) have prepared mutants of the erythropoietin receptor. Mutant receptors are those in which one or more naturally occurring amino acids have been substituted or deleted, or those in which additional amino acids have been added. Some mutants are combinations of substitution, deletion, and/or insertion of amino acids.

One method of studying the mechanism(s) of receptor activation and signaling has been to construct artificial or synthetic receptor molecules. These molecules are generally known as hybrid or chimeric receptors. Such receptors typically possess the extracellular domain of one naturally occurring receptor and the intracellular domain of another naturally occurring receptor. The majority of hybrid receptors that have been generated are intra-familial hybrids, i.e., the intra- and extracellular domains of the hybrid receptor are derived from members of the same family or superfamily of receptors.

Venkitaraman et al. (*Proc. Natl. Acad. Sci. USA*, 89:12083–12087 [1992]) describe hybrid receptor molecules between the CD8 receptor and the interleukin 7 (IL-7) receptor, both of which are members of the cytokine superfamily of receptors.

Adachi et al. (*FEBS Lett.*, 311:179–183 [1992]) describe hybrid receptor molecules of the endothelin A and endothelin B receptors.

Koller et al. (*Mol. Cell. Bio.*, 12:2581–2590 [1992]) describe receptors that are hybrids of naturetic peptide receptor A (NPR-A) and natriuretic peptide receptor B (NPR-B), both of which are members of the guanylyl cyclase receptor family. In addition, hybrid receptors of NPR-A or NPR-B in combination with a portion of the epidermal growth factor receptor (EGFR) or the endotoxin receptor were generated by these researchers, but these hybrids were not stimulated by ligand.

Zon et al., (*Mol. Cell. Biol.*, 12:2949–2957 [1992]) discuss production of hybrid receptors between the erythropoietin receptor (EPOR) and the interleukin 3 (IL-3) receptor. Both of these receptors are members of the cytokine superfamily of receptors.

Fuh et al., (Science, 256:1677–1680 [1992]) describe a hybrid receptor between the extracellular domain of the human growth hormone receptor (hGHR) and the intracellular domain of murine granulocyte colony-stimulating factor receptor (G-CSFR). Both of these receptors are members of the cytokine receptor superfamily.

Seedorf et al., (*J. Biol. Chem.*, 266:12424–12431 [1991]) set forth the production of a hybrid receptor that consists of the extracellular domain of EGFR and the intracellular domain of the platelet derived growth factor receptor (PDGFR). Both of these receptors are members of the protein tyrosine kinase receptor family.

Lev et al. (*Mol. Cell. Biol.*, 10:6064–6068 [1990]) discuss a hybrid receptor between $p145^{kit}$, a protooncogene, and EGFR. Both of these receptors are members of the protein tyrosine kinase receptor family.

Dull et al., U.S. Pat. Nos. 4,859,609 (issued Aug. 22, 1989) and 5,030,576 (issued Jul. 9, 1991) describe hybrid receptors, and set forth specific hybrids between EGFR and the insulin receptor (IR), and between EGFR and HER2-erbB2, an oncogene. EGFR, IR, and HER2-erbB2 are all members of the protein-tyrosine kinase receptor superfamily.

Patent Cooperation Treaty WO 91/06570, published May 16, 1991, sets forth hybrid molecules between the antibody Fc receptor and an antibody. The hybrid molecule is preferably in a soluble form.

Some inter-familial, or heterologous, hybrid receptors have also been generated. Only a few of these have been found to be biologically active, i.e., are capable of transducing a signal from the extracellular environment to the intracellular environment. For example, Yan et al. (*Science*, 252:561–563 [1991]) describe a hybrid receptor molecule containing the extracellular domain of EGFR and the intracellular and transmembrane domains of the human low-affinity nerve growth factor receptor (NGFR). The hybrid was found to induce neurite outgrowth in cells stimulated with EGF; the hybrid was also able to specifically induce a NGF-responsive gene called transin.

Bernard et al. (*Proc. Natl. Acad. Sci. USA*, 84:2125–2129 [1987]) describe a hybrid receptor of the extracellular domain of interleukin 2 (IL-2) and the transmembrane and intracellular domains of EGF. Cells transfected with this hybrid did not respond to ligand added to culture medium, suggesting that the hybrid receptor was not biologically active.

Interfamilial hybrid receptors provide a means for obtaining information about newly identified receptors with unknown ligands. For example, the extracellular domain of a newly identified receptor may be linked to the intracellular domain of a receptor with a known signal transduction mechanism. Various potential ligands can then be tested to identify those that bind to the extracellular domain of the hybrid and are capable of transmitting a signal.

There is a need in the art to provide a means of identifying the ligands of newly discovered receptors. There is a further need in the art to provide hybrid receptors that can be used to increase or decrease cellular responses to certain ligands through the use of agonists and/or antagonists to these receptors.

Accordingly, it is an object of the present invention to provide a hybrid receptor molecule wherein one domain of the hybrid receptor is derived from the cytokine superfamily of receptors, and the other domain of the receptor is derived from a separate and distinct or heterologous family of receptors. Various potential ligands for the molecule can be evaluated for their ability to stimulate or inhibit signaling to the intracellular environment.

SUMMARY OF THE INVENTION

This invention is based on the unexpected discovery that hybrid receptors comprising an extracellular domain from certain members of one receptor family and an intracellular domain from certain members of a heterologous receptor family possess biological activity when DNA encoding the hybrid receptor is transfected into and expressed in cell lines.

In one aspect, this invention provides a biologically active hybrid receptor molecule, wherein one domain of the hybrid is a member of the hematopoietic cytokine receptor family, and the other domain is a member of a separate and distinct family of receptors.

In another aspect, the invention provides a hybrid receptor molecule wherein the extracellular domain is a member of the protein-tyrosine kinase receptor family such as epidermal growth factor receptor (EGFR) and the transmembrane and intracellular domains are members of the hematopoietic cytokine receptor family such as erythropoietin receptor (EPOR).

In yet another aspect, the invention provides a hybrid receptor molecule wherein the extracellular domain is a member of the hematopoietic cytokine receptor family such as EPOR and the transmembrane and intracellular domains are members of the atrial natriuretic peptide receptor (ANPR) family such as ANPRA, ANPRB and ANPRC.

In one other aspect, the invention provides host cells transfected with a DNA sequence encoding the hybrid receptor and expressing a biologically active form of the hybrid receptor on a particular cell membrane.

DETAILED DESCRIPTION OF THE INVENTION

Figure 1:
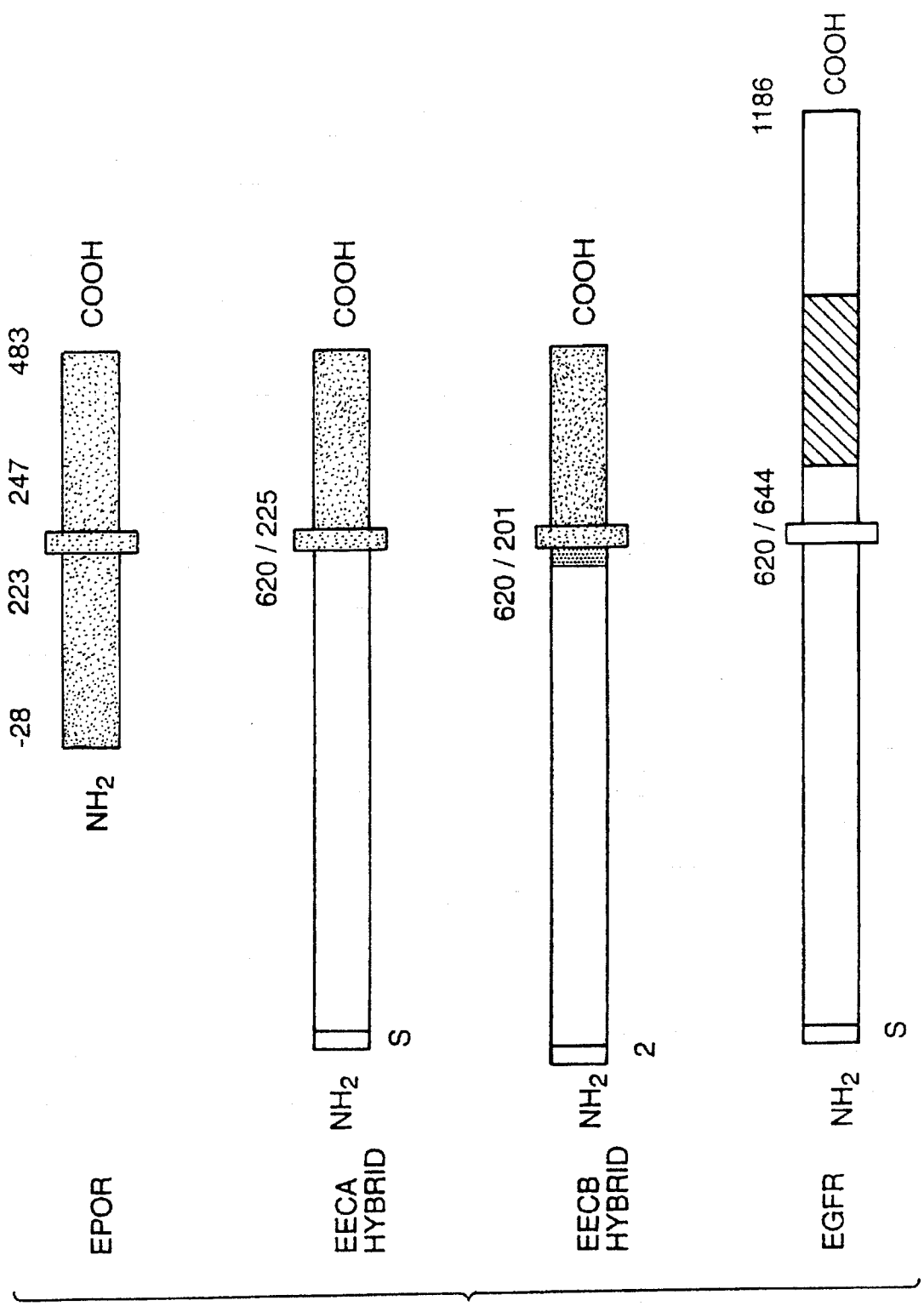
FIG. 1 is a schematic diagram of the erythropoietin receptor (EPOR), the epidermal growth factor receptor (EGFR), and two EGFR-EPOR hybrid receptors called EECA and EECB (described in detail in Example I), that were constructed using the extracellular domain of EGFR and various fragments of the transmembrane and intracellular domains of EPOR. The darkened regions represent EPOR sequences, the darkened vertical bar represents the transmembrane domain, the open regions represent EGFR sequences, the striped region represents the tyrosine kinase domain of EGFR, and the dotted region represents the WSXWS motif of EPOR. The numbers above each receptor construct represent the number of amino acids from that domain that were used in the construct. Negative numbers refer to the signal sequence; number 1 is the first amino acid at the amino terminus of the mature receptor sequence.
Figure 2A:
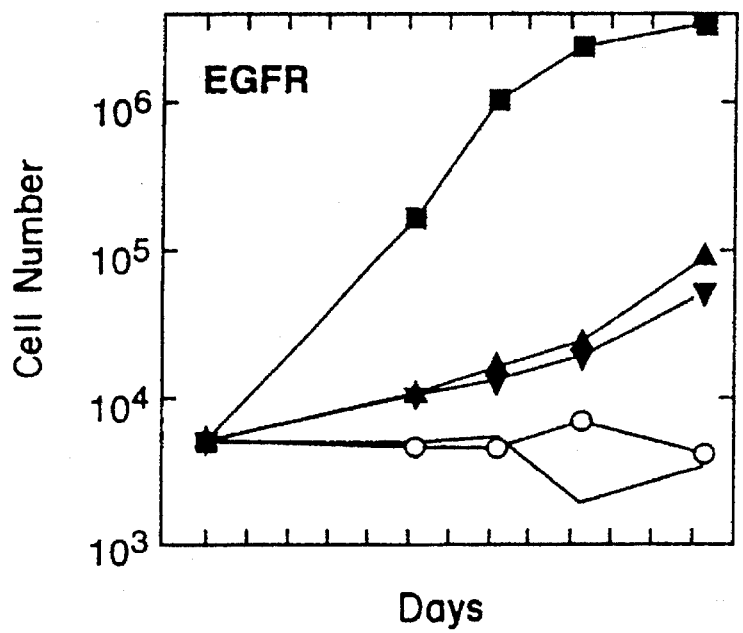
FIG. 2 depicts the sustained growth of murine 32D cells transfected with and expressing various receptor DNA constructs, and grown in the presence of the growth factors IL-3, EGF, TGF-alpha, or EPO. Darkened squares represent IL-3 (interleukin-3), darkened triangles represent EGF (epidermal growth factor), inverted triangles represent TGF-alpha (transforming growth factor alpha), open circles represent EPO (erythropoietin), and the solid line represents no added growth factor.
Figure 2B:
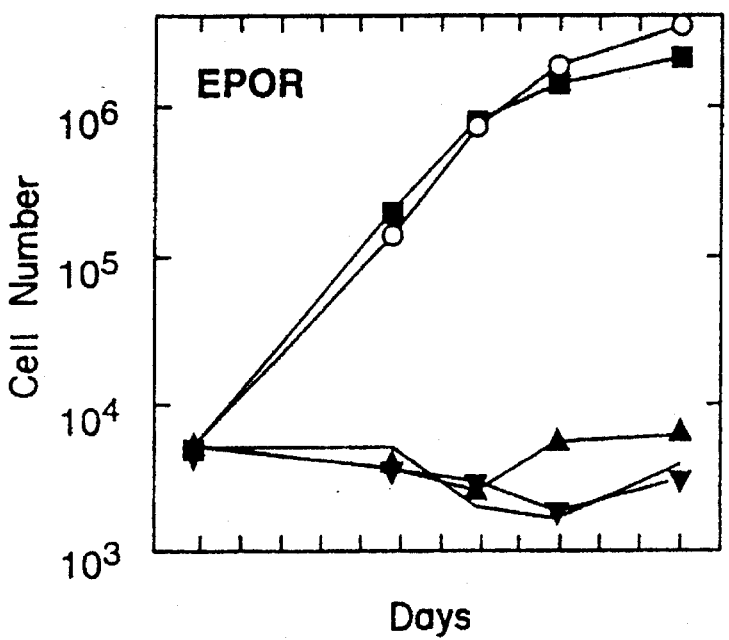
Figure 2C:
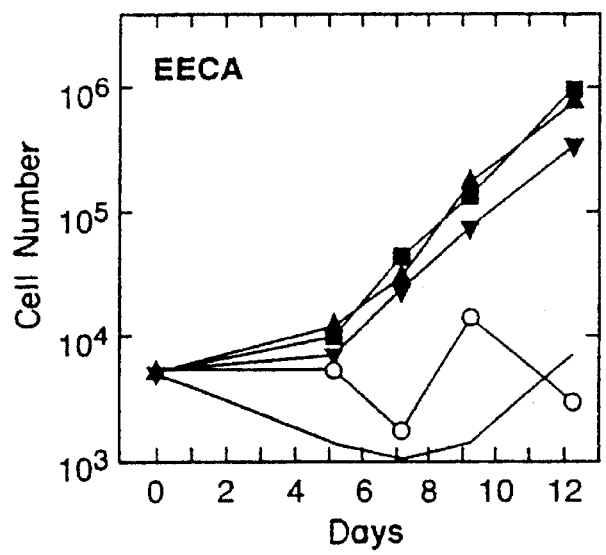
Figure 2D:
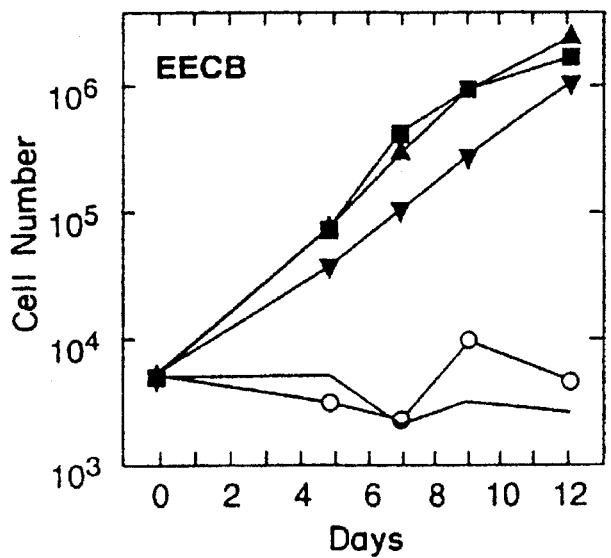
Figure 2E:
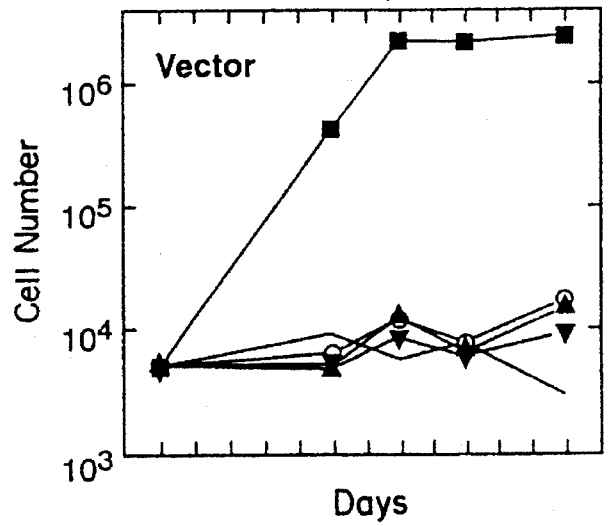

The following terms are used to describe the invention.

The term "receptor" refers to a molecule, typically composed primarily of protein, that is associated, at least transiently, with one or more types of cellular membranes, and has as its main biological function the ability to bind a specific ligand or group of ligands, and, upon ligand binding, to mediate signal transduction, either directly or indirectly, in the cell. The cell from which the receptor is obtained may be any vertebrate cell, invertebrate cell, plant cell, bacterial cell or any other microorganism cell. The receptor may also reside naturally on the coat of any virus. The cellular membrane from which the receptor is obtained may be the plasmalemma (the membrane surrounding the cell) or any intracellular membrane surrounding any cellular organelle, such as the mitochondrial membrane, the chloroplast membrane (inner or outer), the nuclear membrane, the lysosomal membrane, the vacuolar membrane (the tonoplast), the endoplasmic reticulum, and the like. The typical receptor has three portions or domains, namely, an intracellular domain, an extracellular domain, and a transmembrane domain. In addition, the receptor typically has a sequence of about 5–25 amino acids at its amino terminus that serve to target the receptor to the proper membrane. These domains will vary in size and in function from receptor to receptor. Typically, the extracellular domain binds to one or more ligands, the transmembrane domain anchors the receptor into the membrane, and the intracellular domain perceives the binding of ligand and transmits a signal to the interior of the cell (the intracellular environment). Usually, the transmembrane domain of the receptor is comprised primarily of hydrophobic amino acids, while the extracellular domain and the intracellular domain may contain all types of amino acids.

The term "hybrid" refers to the amino acid composition and/or DNA sequence of the receptor. The receptors of this invention are typically combinations of pieces or fragments of naturally occurring receptors, and/or mutants thereof, however the hybrid may be comprised of full-length sequences of any or all of the domains. Typically, the hybrid receptor will be comprised of an extracellular domain, a transmembrane domain, and an intracellular domain. The extracellular domain will be derived from certain members of one family of receptor molecules, while the intracellular domain will be derived from certain members of a second family of receptor molecules. The transmembrane domain may be derived from the same receptor as either the intracellular or extracellular domain, or it may be derived from a third receptor source. In addition, any or all of the domains may be synthetic in origin, i.e., based on sequences that are not naturally occurring.

The terms "heterologous", "heterologous receptor", and "heterologous receptor domain" refer to receptors or receptor domains derived from separate and distinct groups, classes, families or superfamilies of receptors. The hybrid receptor molecules of this invention are heterologous in that one domain of the hybrid receptor is typically derived from one family of receptors, such as for example, the hematopoietic cytokine receptor family, while another domain of the receptor is derived from an unrelated receptor family, such as, for example, the protein-tyrosine kinase receptor family.

The terms "family", "class", and "superfamily" refer to a collection of cell membrane receptors that are considered to have a certain level of homology, either in terms of structure (e.g., a certain level of amino acid or nucleic acid sequence homology), function (e.g., they are all involved in antigen recognition or bind a certain type of ligand), or activity (e.g., they all hydrolyze ATP). Typically, superfamilies comprise more than one class or family of receptors.

The terms "hematopoietic cytokine receptor" and "hematopoietic cytokine receptor family" refer to receptors that have one or more cytokines as their primary ligand(s), although they may have different mechanisms of signaling. As used herein, cytokines are defined as molecules usually comprised primarily of protein, that affect growth and/or differentiation of various cells. Many of the hematopoietic cytokine receptors contain the WSXWS amino acid sequence motif (W represents tryptophan; S represents serine, and X represents a nonconserved amino acid).

The term "ligand" refers to a molecule that binds to a receptor with a certain specificity and affinity. The ligand(s) may be natural or synthetic, and the ligand(s) may have the ability to bind to more than one type of receptor. The ligand may be an inorganic or an organic molecule. The organic molecules may be composed of nucleic acid, protein, lipid, carbohydrate, or any other type of organic molecule combination thereof.

The term "biologically active" refers to hybrid receptors that are (1) capable of binding one or more ligands, and (2) able to respond to the binding by signaling the cell, either directly or indirectly in a manner that is detectable and is distinct from the response of cells not transfected with DNA encoding the hybrid receptor. The response of the receptor to the ligand binding will be detectable by assaying for signaling, such as by a conformational, chemical, or structural change in the receptor (for example, phosphorylation of the receptor), dimerization of the receptor with another molecule, production of a chemical messenger on the surface of or inside of the cell (such as cGMP), immunological detection, growth and/or differentiation, or other assay that is appropriate for the particular hybrid receptor being evaluated.

Methods of Making the Invention

1. Selection of Receptor Extracellular Domain

The extracellular domain of the hybrid receptor may be any naturally occurring amino acid sequence, or a synthetic amino acid sequence that is known or is believed to be the extracellular domain of a receptor. Such amino acid sequences are encoded by naturally occurring or synthetic DNA sequences. In addition, the extracellular domain may be one or more fragments or pieces of receptor extracellular domain sequences derived from more than one family of receptors. Included within the scope of this invention are newly identified sequences believed to be receptor or membrane bound sequences with no known function.

The extracellular domain may be derived from any bacterial receptor, vertebrate or invertebrate receptor, plant receptor, or a receptor from any other source; the receptor may naturally be found on the plasmalemma of a certain cell type(s) or on a membrane that surrounds a cellular organelle such as, for example, the endoplasmic reticulum, the nucleus, a lysosome, a vacuole, a mitochondrion, or a chloroplast. The extracellular receptor amino acid sequence may be a fragment and/or a mutant form of the known sequence from which it is derived. For purposes herein, a mutant is defined as a polypeptide encoded by a DNA sequence containing any alteration in the native DNA sequence, whether it be nucleotide insertions, deletions, or substitutions. In addition, changes in the carbohydrate composition of the polypeptide (including alterations of the sugar residues of the carbohydrate linkage, and/or addition or subtraction of carbohydrate moieties on the polypeptide as compared with the native sequence) are considered herein to be mutations.

The extracellular domain may be a hybrid molecule in and of itself, i.e., it may be composed of fragments or sequences derived from more than one receptor extracellular domain.

Where the extracellular domain is a fragment of an extracellular domain full length sequence, the fragment will typically include the known or putative ligand binding region of the extracellular domain, as well as any other region of the extracellular domain that is believed to be at least partially responsible for the biological activity of the receptor from which it is derived.

Typically, the extracellular domain will contain, usually at its amino terminus, a sequence of about 5–25 amino acids that direct the receptor molecule to the proper membrane after the receptor is synthesized in the cell. Such sequences usually are known as signal sequences or leader peptides.

This invention contemplates the use of primarily two types of extracellular domains: those with known ligands, and those with no known ligands. Production of hybrid receptors that have extracellular domains with known ligands will be useful for a variety of functions, but especially for screening new ligands that are believed to either enhance the level of intracellular signaling, or to decrease or inhibit intracellular signaling.

Production of hybrid receptors with extracellular domains for which no known function and/or ligand exists will be useful for identifying the ligands and/or functions of the novel extracellular domain(s). Once the ligands have been identified, one may obtain information on the receptor's inherent activity. In addition, novel ligands that bind to the receptor then can be screened to evaluate their potential for increasing or decreasing receptor activity.

Typically, the extracellular domain will be selected from a receptor whose inherent activity either confers a beneficial or a detrimental function upon cellular homeostasis; the objective will be to identify ligands that increase the activity of this receptor thereby enhancing the beneficial effects of the receptor, or decrease its activity where the receptor's activity is known to be or is believed to be detrimental to the cell.

Preferred extracellular domains of this invention are those with no known function and/or ligand, but with some homology, either at the nucleic acid or amino acid level, to any domain of a known receptor. By way of example, a preferred extracellular domain is encoded by a cloned DNA sequence of unknown function that has sequence homology with the DNA encoding the intracellular kinase domain of a protein tyrosine kinase receptor, or a cloned DNA sequence that has sequence homology with the WSXWS motif that is present in many members of the cytokine receptor family. Other preferred extracellular domains of this invention include those of the protein tyrosine kinase family such as epidermal growth factor receptor and its homologs, the erythropoietin receptor and its homologs, other members of the hematopoietic cytokine receptor family and homologs, the atrial natriuretic peptide receptors, such as ANPRA (Lowe et al., *EMBO J.*, 8:1377–1384 [1989]), ANPRB (Chang et al., *Nature,* 341:68–72 [1989]), or ANPRC, and their homologs, granulocyte-colony stimulating factor receptor and its homologs, and human fetal liver kinase-2 receptor and its homologs.

If the intracellular domain of the hybrid receptor is not a member of the hematopoietic cytokine receptor family, then the extracellular domain will be selected from this family.

2. Selection of Receptor Intracellular Domain

The intracellular domain of the hybrid receptor will be obtained from a receptor family that is separate and distinct from the extracellular domain receptor family. Typically, this domain will be selected based on its ability to produce or to transmit a detectable response in cells expressing this domain when ligand is added to the cell culture medium. However, the intracellular domain from any receptor may be used. The intracellular domain may be derived from a bacterial receptor, a vertebrate or invertebrate receptor, a plant receptor, or a receptor from any other source; the receptor may naturally be found on the plasmalemma of a certain cell type(s) or on a membrane that surrounds a cellular organelle such as, for example, the endoplasmic reticulum, the nucleus, a lysosome, a vacuole, a mitochondrion, or a chloroplast. The intracellular receptor DNA and/or amino acid sequence may be a fragment and/or a mutant form of the known sequence from which it is derived. For purposes herein, a mutant is defined as a polypeptide encoded by a DNA sequence containing any alteration in the native DNA sequence, whether it be nucleotide insertions, deletions, or substitutions. In addition, changes in the carbohydrate composition of the polypeptide (including alterations of the sugar residues of the carbohydrate linkage, and/or addition or subtraction of carbohydrate moieties on the polypeptide as compared with the native sequence) are considered to be mutations.

The intracellular domain may be a hybrid molecule in and of itself, i.e., it may be composed of fragments or sequences derived from more than one receptor intracellular domain, provided that the domain is constructed in such a manner as to be functional in signal transduction.

Preferred intracellular domains are those with a known and assayable signal transduction mechanism or activity such as, for example, the erythropoietin receptor intracellular domain, the granulocyte-colony stimulating factor receptor, the granulocyte macrophage colony stimulating factor receptor, the epidermal growth factor receptor intracellular domain, or the atrial natriuretic peptide receptor type A (Lowe et al., *EMBO J.*, 8:1377–1384 [1989]), type B (Chang et al., *Nature,* 41:68–72 [1989]), or type C intracellular domain.

If the selected extracellular domain of the hybrid receptor is not a member of the hematopoietic cytokine receptor family, then the intracellular domain of the hybrid receptor will be selected from the hematopoietic cytokine receptor family. Where the extracellular domain has no known activity, and thus it is unclear whether it is a member of the hematopoietic cytokine receptor family, the intracellular domain may be a member of this family.

3. Selection of Receptor Transmembrane Domain

The transmembrane domain sequence of the hybrid receptor may be obtained from any source. Typically however, it will be selected from the same receptor as either the intracellular domain or the extracellular domain. However, the transmembrane domain may also be selected from a receptor that is a member of a separate and distinct group from either the extracellular domain receptor or the intracellular domain receptor. While the main purpose of the transmembrane domain appears to be to anchor the receptor into the membrane, this domain may also be important in certain receptors for signal transduction. Thus, it may be necessary that the transmembrane domain be of the same origin as either the extracellular domain or intracellular domain, depending on the predicted or known mechanism of signaling.

4. Hybrid Receptor Preparation

The hybrid receptors of this invention are typically prepared using recombinant DNA technology. A DNA construct containing the DNA sequences of the selected intracellular, extracellular, and transmembrane domains is prepared, usually by isolating the desired cDNA sequences for each domain of the hybrid receptor, using methods well known in the art. These methods include, without limitation, polymerase chain reaction (PCR) which is particularly useful where at least a partial sequence of the gene of interest is known; and cDNA and/or genomic library screening with suitable probes (usually oligonucleotides and/or antibodies for cDNA libraries, and oligonucleotides or cDNA sequences for genomic libraries). Some of these methods as well as other methods useful for molecular cloning are set forth by Sambrook et al. (*Molecular Cloning: A Laboratory Manual,* Cold Spring Harbor Laboratory Press, Cold Spring Harbor, N.Y. [1989]).

After the DNA sequences for each of the domains have been obtained in suitable quantities, they are ligated in the proper orientation, thereby producing a single DNA construct encoding the intracellular, transmembrane, and extracellular domains of the desired hybrid receptor. The ligation may be done with several DNA fragments simultaneously, or it may be done in successive steps. In addition, one fragment of DNA may first be ligated into a vector, after which time the other fragment(s) of DNA are then ligated into the same vector at the correct position.

In some cases, it may be necessary to first make the ends of each DNA fragment compatible for ligation to each other. This is done by either blunting the ends of each of the DNA fragments, or cutting the ends with appropriate restriction endonucleases. Both of these methods are described in Sambrook et al., supra. This single construct is then ligated into a suitable vector (unless the DNA fragments of interest were previously ligated into the vector one at a time) for transfection into selected cells.

The DNA encoding the hybrid receptor will typically be placed into a vector for amplification and for expression in the host cells. Any eukaryotic expression vector may be used when the hybrid receptor is to be expressed in eukaryotic cells. Prokaryotic expression vectors will be used for expression in bacterial cells. Selection of the expression vector will depend on several factors such as the choice of restriction endonuclease sites in the polylinker region of the vector, the type of promoter, and the selectable marker. Preferred promoters are those that yield a high level of transcription in a variety of host cells such as a retrovirus promoter (e.g. the cytomegalovirus promoter). Preferred selectable markers are neomycin, hygromycin, ampicillin, tetracycline, and other antibiotic resistance markers. Preferred vectors are pRc/CMV and pRc/RSV (both available from InVitrogen, San Diego, Calif.), pXT 1 (Stratagene, San Diego, Calif.) and pLJ (Korman et al., *Proc. Natl. Aced. Sci. USA,* 84:2150–2154 [1987]).

While recombinant DNA methods are the usual means for preparing hybrid receptors, other methods useful for preparation of these receptors may be employed as well. Such methods include, for example, chemical and/or enzymatic synthesis of either the amino acid or DNA sequence of the hybrid receptor, using methods well known in the art.

5. Expression of the Hybrid Receptor

The hybrid receptor DNA vector construct may be transfected into a selected cell line for expression and evaluation of receptor activity. Transfection can be accomplished using any known method, including without limitation, the calcium phosphate procedure, electroporation, viral infection (via the use of retroviruses), lipofection, DEAE-dextran, or microinjection. The transfection method used will depend in part on the cell type being transfected. For bacterial cells, electroporation is generally preferred. For mammalian cells, transfection can be accomplished using electroporation, or alternatively, the DEAE-dextran method as described in Section 9.2 of Ausubel et al., eds. (*Current Protocols in Molecular Biology,* Greene and John Wiley and Sons, New York [1987]).

Selection of host cell lines for incorporation and expression of the hybrid receptor DNA will normally depend on the hybrid receptor to be evaluated. In some cases, the cell line selected will be one that does not express, at very high levels, the naturally occurring receptors from which the hybrid was constructed, and preferably one that does not express such receptors at all. In addition, the selected cell line preferably will be one that does not naturally produce a significant amount of the ligand or ligands to be screened. In some cases, i.e., where growth is the end-point of the signal transduction process, the preferred cell line will be one that is dependent for growth and/or survival on one or more growth factors that the cells do not produce endogenously and that are not present in serum, but that can be added exogenously to the cell culture medium. In this type of system, the factor can be removed from the cell culture medium, and then only cells stimulated by the hybrid receptor ligand will grow.

Preferred cell lines for use in this invention are murine 32D cells (ATCC No.CRL 11346, deposited May 13, 1993 with the American Type Culture Collection ["ATCC"], 12301 Parklawn Drive, Rockville, Md. 20852, U.S.A.), COS-1 and COS-7 cells (African Green monkey kidney cells, ATCC Nos. CRL 1650 and CRL 1651, respectively), CBT6 cells (Pan et al., *Virol.,* 125:1–7 [1983]), TF-1 cells (Kitamura et al., *J. Cell. Physiol.,* 140:323–334 [1989]), FDC-P1 cells (Spooncer et al., *Nature,* 310:228–230), HEL cells (human erythroleukemia cells, ATCC No. TIB 180), and Ba/F3 cells (Palacios et al., *Cell,* 41:727–734).

In addition to expressing the hybrid receptor molecules in cultured cells, the receptors may be expressed in vivo in a variety of animals such as mice or other rodents, using standard procedures known in the art such as those set forth in Hogan et al., eds., *Manipulating the Mouse Embryo: A Laboratory Manual* (Cold Spring Harbor Laboratory Press, Cold Spring Harbor, N.Y. [1986]).

6. Hybrid Receptor Activity Assays

After transfection of the host cell line, the cells can be screened for incorporation of the hybrid receptor DNA into the nucleus and/or for expression of the hybrid receptor on the cell membrane.

Incorporation of the hybrid receptor DNA into the nucleus can be analyzed by Southern blotting total nuclear DNA of the host cell, and probing this blot with a probe designed to specifically detect a portion of the hybrid receptor DNA sequence. Other methods of detecting incorporation of DNA into the nucleus include, for example, polymerase chain reaction (PCR), and probe protection using a radioactive DNA or RNA probe that is hybridized to the DNA of interest on a Southern blot.

Expression of the hybrid receptor polypeptide can be evaluated in a variety of ways. To measure the level of hybrid receptor protein in the cell, an antibody directed against particular regions of the hybrid receptor may be used in either a Western blot analysis or in an immunoprecipitation analysis. Expression may also be monitored using fluorescence activated cell sorting (FACS). Alternatively, or additionally, bioassays to detect the activity of the hybrid receptor may be used. Here, the ligand or suspected ligand is added to the cell culture along with other reagents as necessary for analyzing receptor activity (for example, $^{32}$P-ATP, $^3$H-thymidine, $^{32}$P-GTP, and the like); after an appropriate period of time, the cells are assayed for certain changes that may have occurred in response to ligand binding. Some of these changes may include for example, phosphorylation of the receptor itself or of another protein, production of cGMP or cAMP, or expression of particular genes in the cell. In addition, the rate of host cell proliferation or the rate of host cell death may be a means of measuring hybrid receptor activity.

To measure the level of hybrid receptor mRNA in the host cell, Northern blot analysis, RNase protection assays, and/or reverse transcriptase/PCR assays can be conducted.

7. Screening for Receptor Ligands

One key feature of the hybrid receptors provided in this invention is their use in screening for novel ligands that may either increase or decrease the level of signaling in the cell. In addition, these receptors can provide a means of producing a signal in a cell that might not normally receive a signal in response to a certain ligand.

The ligand(s) to be tested can be added to the transfected host cell culture media at several concentrations over various periods of time, and binding can be assessed by the use of one or more assays designed to detect ligand binding as discussed above.

Where the hybrid receptor is expressed in transgenic mammals, the ligand to be evaluated would be administered to the mammal over a wide range of doses. The effects of the ligand on the mammal could then be tested using suitable in vitro assays (by extracting and analyzing tissues expressing the hybrid receptor) or by in vivo evaluations.

The invention will be more fully understood by reference to the following examples. These examples should not be construed in any way as limiting the scope of the invention.

EXAMPLE I: PRODUCTION OF AN EGFR-EPOR HYBRID RECEPTOR

1. Cell preparation

Cell cultures of the murine cell line 32D clone 3 (deposited with the ATCC as accession no ATCC# CRL 11346, deposited May 13, 1993) were used in this study. This cell line was selected for its dependence for growth and survival on interleukin-3 (IL-3). In addition, this cell line does not endogenously produce detectable levels of either the erythropoietin receptor (EPOR) or the epidermal growth factor receptor (EGFR).

The cells were cultured in Standard Medium consisting of RPMI 1640 medium (Gibco/BRL, Grand Island, N.Y.) supplemented with 10% heat inactivated fetal bovine serum (Hyclone, Logan, Utah) and 100 pg/ml recombinant murine interleukin 3 (IL-3; Peprotech, Rockyhill, N.J.). The cultures were kept in an incubator at 37° C. and 5% $CO_2$, and were routinely passaged by dilution into fresh medium about once per week to maintain the density between $10^4$ and $10^6$ cells/ml.

2. DNA Constructs

Two EGFR/EPOR hybrid receptor DNA constructs were prepared. The receptors encoded in these constructs are depicted in FIG. 1. Both of the hybrids contained the extracellular domain of EGFR from amino acids −24 to 620 (where −24 through −1 are the signal sequence amino acids for EGFR; see Linet al., *Science*, 224:843–848 [1984]; SEQ ID NO:9). One of the hybrids, called EECA, contained the transmembrane and cytoplasmic domain of murine EPOR, spanning from amino acids 225–483 of EPOR (SEQ ID NO:10). The other hybrid, EECB, contained a larger portion of the murine EPOR sequence and included the highly conserved amino acid motif WSXWS (W=tryptophan; S=serine; X is any amino acid), which is the first portion of the extracellular domain of EPOR. This hybrid receptor contained amino acids 201–483 of EPOR.

Human EGFR cDNA was obtained from a human placenta library prepared in the pSPORT vector (Gibco/BRL, Grand Island, N.Y.) by probing the library with a 400 base pair cDNA probe. The cDNA probe was obtained by PCR amplification of a 400 base pair fragment of an EGFR cDNA sequence. The PCR probes were selected based on the published EGFR sequence (Linet al., *Science*, 224:843–848 [1984]). These probes are set forth below:

Probe 1 (SEQ ID NO:1):

5'-AAGATCAAAGTGCTGGGCTCCGGT-3'

Probe 2 (SEQ ID NO:2):

5'-ATGGTATTCTTTCTCTTCCGC-3'

The murine EPOR full length cDNA sequence was obtained as follows: Human fetal liver mRNA (Clonetech, Palo Alto, Calif., catalog number 6527-2) was reverse transcribed into cDNA using reverse transcriptase and a primer based on the published sequence of human EPOR (Jones et al., *Blood*, 76:31–35 [1991]). The cDNA was amplified using PCR and specific primers for the 3' and 5' regions of the cDNA based on the same EPOR published sequence. The EPOR sequence was inserted into the vector PRC/CMV (InVitrogen Corp, San Diego, Calif.; catalog number V750-20).

The EECA construct was prepared using a two step PCR (polymerase chain reaction) technique as described by Higuchi (*PCR Protocols: A Guide to Methods and Applications*, M. Innis et al., eds. Academic Press, New York, pp. 177–183 [1989]). For all PCR reactions, 75 ng of cDNA template was added to 100 µl of PCR reaction mix containing 1 unit of Deep vent polymerase (New England Biolabs, Beverly, Mass.), 1×Deep vent buffer, 200 µM of each nucleotide triphosphate and 20 pmol of each primer. Each reaction was cycled 20 times.

The first step of this process was conducted to obtain the appropriate cDNA fragments of both EGFR and EPOR. The following primers were used with EGFR cDNA as a template to obtain the EGFR extracellular domain linked to a portion of EPOR:

Primer A (SEQ ID NO:3):

5'-GCCAACGCCACAACCACCGCGCGCGGC-CGCCTGACTCCG-3'

Primer B (SEQ ID NO:4):

5'TGAGAGACAGCGTCAATATTAGCGG-GATCTTAGGCCCATT-3'

Primer A corresponds to nucleotides −86 to −48 of the coding strand of EGFR with the exception of nucleotides −58 and −64 which were changed from C to G to generate a NotI restriction site. Primer B corresponds to nucleotides 768–747 of the non-coding strand of EPOR and nucleotides 1932–1915 of the non-coding strand of EGFR, with the exception of nucleotides 749 and 752 which were both changed to A to generate a SspI restriction site. The cycle sequence for PCR was 96° C. for 15 sec., 68° C. for 30 sec., and 72° C. for 2 minutes.

To obtain the appropriate portion of EPOR intracellular domain cDNA for this hybrid receptor, the following two primers were used in the first step of the PCR process:
Primer C (SEQ ID NO:5):

5'-AATGGGCCTAAGATCCCGCTAATAT-TGACGCTGTCTCTCA-3'
Primer D (SEQ ID NO:6):

5'-AGCAGCCACAGCTGGAAGTTAC-3'

Primer C is the complement to primer B, and primer D corresponds to EPOR sequence downstream of a unique BglII restriction site. For generation of this DNA fragment, the PCR cycle sequence was 96° C. for 15 sec., 64° C. for 30 sec., and 72° C. for 1 minute.

The DNA fragments from each of the above PCR reactions were purified using standard agarose gel electrophoresis methods for extraction and purification. The second step of the two-step PCR process was then conducted with these DNA fragments and primers A and D above. The PCR cycle sequence for this step was 96° C. for 15 sec., 64° C. for 30 sec., and 72° C. for 2 minutes.

The EECB construct was prepared using the same two-step PCR procedure (Higuchi, supra) under the same reaction conditions as set forth above. Four primers were used to generate the appropriate cDNA fragments.

To obtain the EGFR extracellular domain sequence, primer A (set forth above) was used with primer E and the EGFR cDNA for PCR amplification.
Primer E (SEQ ID NO:7)

5'-ACTCCAGAATCCGCTGAAGCTCGG-GATCTTAGGCCCATT-5'

For this reaction, the PCR cycle sequence was 96° C. for 15 sec., 68° C. for 30 sec., and 72° C. for 2 minutes To obtain the EPOR intracellular domain including the WSXWS extracellular motif, EPOR cDNA was used with primer D (set forth above) and primer F. Primer F is the complement to primer E.
Primer F (SEQ ID NO:8)

5'-AATGGGCCTAAGATCCCGAGCTTCAGCG-GATTCTGGAGT-3'

For this reaction, the PCR cycle sequence was 96° C. for 15 sec., 64° C. for 30 sec., and 72° C. for 2 minutes.

The second step of the two-step PCR process to generate the EECB construct was performed using the DNA fragments (agarose gel purified) from the two primary reactions in conjunction with primers A and D. The PCR cycle sequence was 96° C. for 15 sec., 64° C. for 30 sec., and 72° C. for 2 minutes.

The hybrid receptor DNA constructs EECA and EECB were assembled using standard ligation methods into the vector pUC19 (New England Biolabs, Beverly, Mass.). The vectors containing the inserts were then transformed into *E. coli* cells strain DH5 alpha for amplification. The plasmids were then purified using Qiagen columns (Qiagen, Chatsworth, Calif.) and the inserts were subcloned into the vector pLJ (also referred to as DOL$^-$; Korman et al., *Proc. Natl. Acad. USA*, 84:2150–2154 [1987]). This vector contains a neomycin resistance gene which affords selection for transformants using the antibiotic G418.

3. DNA Construct Transfection

The EECA and EECB constructs were transfected into the cultured 32D cells using the technique of electroporation. Prior to electroporation, the cells were grown to a density of about $1 \times 10^6$ cells per ml and harvested by centrifugation at about 2,000 rpm in a clinical centrifuge for about 10 min.

Next, the cells were washed twice by resuspending them in about 50 ml of electroporation medium (RPMI 1640, plus 10 ng/ml IL-3 and 10 mM HEPES buffer). After washing, the cells were resuspended in electroporation media at a density of about $1.25 \times 10^7$ cells/ml. About 0.8 ml of the resuspended solution of cells (0.8 ml was about $10^7$ cells) were transferred to a 4 mm electroporation cuvette (BioRad Laboratories, Richmond, Calif.). The cuvette was placed on ice. About 20 µg of each DNA construct, prepared as described above using Qiagen columns (Qiagen, Chatsworth, Calif.) was added to cells and mixed gently. Each cuvette of cells was transfected with one construct. The electroporations were carried out using the Biorad Gene Pulser electroporation apparatus at about 25 µF and 1.2 kV, following the manufacturer's instructions. Immediately after electroporation, the cuvettes were placed on ice for 5–10 minutes. The cells were then gently pipetted into 100 mm Falcon petri dishes containing 25 ml of prewarmed Standard Medium. These cells were then placed in an incubator at 37° C. and 5% $CO_2$ overnight After the incubation, the cells were collected by centrifugation by spinning in a table top centrifuge at 2,000 rpm for about 10 min at room temperature. The pelleted cells were then resuspended in 25 ml of a Selective Medium which was Standard Medium plus 750 µg/ml G418 (Geneticin, obtained from Gibco/BRL, Grand Island, N.Y.). Approximately 1 ml of these transfected cells were plated out in each well of 24 well Falcon plates and incubated at 37° C. in 5 % $CO_2$. After 24 hours, each well was topped off with an additional 1 ml of Selective Medium, and the cells were then returned to the incubator. Those cells that had been transformed with the various DNA constructs could be identified after about one and one half to two weeks of culturing by cell colony formation in the wells. Approximately 1 in 1000 cells were transformed. All cells transformed with the same DNA were pooled and passaged in Selective Medium as described above.

4. Hybrid Receptor Activity Assay

To identify those cells expressing the hybrid receptors on the plasma membrane, the cells were either analyzed by fluorescent activated cell sorting (FACS), or by growth factor selection, or by both methods.

The cells to be sorted by FACS were prepared by washing twice in a standard solution of phosphate buffered saline supplemented with 2% fetal calf serum (Gibco/BRL, Grand Island, N.Y.). This solution was called PBSS. The cells were incubated with a first monoclonal antibody, called Ab1, which is directed to the $NH_2$-terminus of EGFR (Antibody Ab1; obtained from Oncogene Sciences, Manhasset, N.Y.). Ab1 was diluted in PBSS to a concentration of 2.5 µg/ml, and 40 ml of this antibody solution was added to the cells to give a final density of about $1 \times 10^6$ cells per ml. The cells were incubated with this antibody for 1 hour at 4° C. Excess Ab1 and/or non-specific binding of Ab1 was eliminated by washing the cells twice in 50 ml of PBSS. Binding of this antibody was visualized with a second antibody directed to Ab1. This second antibody was a goat-anti-mouse IgG fluorescein isothiocyanate conjugated antibody (Southern Biotechnology Associates, Birmingham, Ala.). About 40 ml of this antibody at a concentration of 2.5 µg/ml was added to the cells, and the cells were incubated at about 4° C. for about 1 hour. After the incubation, the cells were washed as above in PBSS. The cells were sorted using a Becton Dickinson FACS-Star Plus (San Jose, Calif.) following the manufacturer's guidelines. Sorting was based on the relative fluorescense of transfected cells as compared to untransfected cells. The sorted cells were allowed to recover in normal medium.

Growth factor selection of the cells was a second means used to enrich for those cells expressing the transfected hybrid receptor DNA. Both FACS sorted cells (transfected with either EGFR DNA, EECA DNA, or EECB DNA) and unsorted cells (transfected with EPOR DNA) were depleted of IL-3 by washing the cells twice in a standard solution of PBS followed by a 3 hour incubation in RPMI-1640 at 37° C. Finally, the cells were washed again in PBS. After washing, the cells were seeded into 6 well cell culture plates at a concentration of about $5 \times 10^4$ cells/ml in RPMI-1640 supplemented with 10% heat inactivated calf serum in the absence of added factors or in the presence of either 100 ng/ml IL-3, recombinant TGF-alpha at 100 ng/ml, recombinant human erythropoietin at 100 µg/ml (Epogen® erythropoietin, Amgen Inc., Thousand Oaks, Calif.) or recombinant human epidermal growth factor at 100 ng/ml (EGF, Amgen Inc., Thousand Oaks, Calif.). Cell growth was monitored over time by sampling the cultures about every other day and counting the cells with an automated Coulter cell counter.

The activity of the hybrid receptors is shown in FIG. 2. A large proportion of the cells expressing either the EPO receptor or the EGF receptor constructs were able to grow in the absence of IL-3 when EPO or EGF, respectively, were added to the growth medium. Wild-type cells and those cells transfected with control DNA only could not survive in the absence of IL-3. The EECA and EECB constructs were able to grow and survive in the absence of IL-3 when EGF was added to the culture medium.

All literature cited herein is specifically incorporated by reference.

We claim:

1. A nucleic acid having a nucleotide sequence encoding a biologically active hybrid receptor consisting of a nucleic acid encoding amino acids −24 to 620 of EGFR (SEQ ID NO:9) linked at its 3' end to the 5' end of a nucleic acid encoding amino acids 225 to 483 of EPOR (SEQ ID NO:10), or a nucleic acid which is fully complementary to said biologically active hybrid receptor encoding-nucleic acid.

2. An expression or amplification vector comprising a nucleic acid having the nucleotide sequence of claim 1.

3. A eukaryotic host cell transfected with a nucleic acid having the nucleotide sequence of claim 1.

4. The host cell of claim 3 that is a 32D cell.

5. The eukaryotic host cell of claim 3 that is a COS-7 cell.

* * * * *